(12) United States Patent
Alanine et al.

(10) Patent No.: US 6,339,093 B1
(45) Date of Patent: Jan. 15, 2002

(54) ISOQUINOLINE DERIVATIVES

(75) Inventors: Alexander Alanine, Riedisheim; Serge Burner, Durmenach-Ferrette, both of (FR); Bernd Buettelmann, Schopfheim (DE); Marie-Paule Heitz Neidhart, Hagenthal le Bas (FR); Georg Jaeschke, Basel (CH); Emmanuel Pinard, Linsdorf (FR); René Wyler, Zurich (CH)

(73) Assignee: Hoffmann-la Roche Inc., Nutley, NJ (US)

( * ) Notice: Subject to any disclaimer, the term of this patent is extended or adjusted under 35 U.S.C. 154(b) by 0 days.

(21) Appl. No.: 09/669,648

(22) Filed: Sep. 26, 2000

(30) Foreign Application Priority Data

Oct. 8, 1999 (EP) .............................. 99120131

(51) Int. Cl.$^7$ ...................... A61K 31/47; C07D 217/02; C07D 215/38; C07D 215/12
(52) U.S. Cl. ........................ 514/307; 514/314; 546/144; 546/159; 546/171; 546/176
(58) Field of Search ................. 546/144, 159, 546/171, 176; 514/307, 314

(56) References Cited

U.S. PATENT DOCUMENTS 5,304,554 A * 4/1994 Strekowski et al. ........ 548/144

FOREIGN PATENT DOCUMENTS

| EP | 343 560 | 11/1989 | |
| WO | WO 97/23458 | 7/1997 | ................. 514/307 |

OTHER PUBLICATIONS

Journal of Neurochemistry, vol. 70, No. 5, pp. 2147–2154 (1998).

* cited by examiner

*Primary Examiner*—Alan L. Rotman
*Assistant Examiner*—Raymond Covington
(74) *Attorney, Agent, or Firm*—George W. Johnston; Dennis P. Tramaloni

(57) ABSTRACT

The present invention relates to compounds of the formula

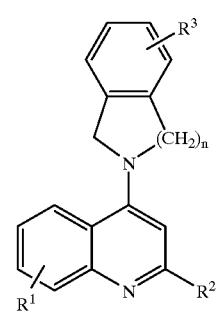

I wherein $R^1$ is hydrogen, lower alkyl, lower alkoxy, hydroxy, amino, nitro, cyano, lower alkyl-amino, di-lower alkyl-amino or halogen;

$R^2$ is hydrogen, lower alkyl, amino, pyrrolidin-3-ol, pyrrolidin-2-yl-methanol or —NHCH$_2$CHROH;

$R^3$ is hydrogen or halogen;

R is hydrogen, lower alkyl or —CH$_2$OH;

n is 1 or 2;

and to pharmaceutically acceptable acid addition salts thereof which are are NMDA(N-methyl-D-aspartate)-receptor subtype selective blockers.

15 Claims, No Drawings

ISOQUINOLINE DERIVATIVES

BACKGROUND OF THE INVENTION

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, chronic and acute pain.

SUMMARY OF THE INVENTION

The present invention relates to compounds of the formula

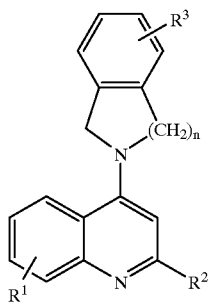

I wherein
$R^1$ is hydrogen, lower alkyl, lower alkoxy, hydroxy, amino, nitro, cyano, lower alkyl-amino, di-lower alkyl-amino or halogen;
$R^2$ is hydrogen, lower alkyl, amino, pyrrolidin-3-ol, pyrrolidin-2-yl-methanol or —NHCH$_2$CH(OH)R;
$R^3$ is hydrogen or halogen;
R is hydrogen, lower alkyl or —CH$_2$OH;
n is 1 or 2;
and to pharmaceutically acceptable acid addition salts thereof.

The compounds of formula I and their salts are distinguished by valuable therapeutic properties. Compounds of the present invention are NMDA(N-methyl-D-aspartate)-receptor subtype selective blockers. NMDA receptors have a key function in modulating neuronal activity and plasticity which makes them key players in mediating processes underlying development of CNS as well as learning and memory function. However when overactive, NMDA receptors contribute to neurodegeneration. Therefore compounds which block NMDA receptor activation are therapeutically important. The compounds of this invention are NMDA receptor blockers, thus have activity in reducing neurodegeneration related to NMDA activity. Such conditions include stroke or brain trauma, chronic forms of neurodegeneration such as Alzheimer's disease, Parkinson's disease, Huntington's disease, ALS (amyotrophic lateral sclerosis) and neurodegeneration associated with bacterial or viral infections, and, in addition, chronic and acute pain. These conditions can result in NMDA mediated neurodegeneration, which neurodegeneration can be treated or prevented by compounds which block NMDA receptors such as the compounds of this invention.

Objects of the invention are the compounds of formula I and pharmaceutically acceptable acid addition salts thereof, the preparation of the compounds of formula I and salts thereof, medicaments containing a compound of formula I or a pharmaceutically acceptable acid addition salt thereof, the manufacture of such medicaments and the use of the compounds of formula I and their pharmaceutically acceptable salts in the control or prevention of illnesses, especially of illnesses and disorders of the kind referred to earlier, and, respectively, for the manufacture of corresponding medicaments.

The present invention embraces racemic mixtures and all their corresponding enantiomers.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain alkyl group containing from 1 to 4 carbon atoms, for example, methyl, ethyl, propyl, isopropyl, butyl and the like.

The term "lower alkyl-amino" denotes an amino group which is substituted by one lower alkyl group. Examples are methylamino, ethylamino and the like.

The term "di-lower alkyl-amino" denotes an amino group which is substituted by two lower alkyl groups which may be the same or different. Examples are dimethylamino, diethylamino, methylethylamino, and the like.

The term "lower alkoxy" denotes a group linked via an oxygen wherein the alkyl residue is as defined above.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, former acid, fumaric acid, maleic acid, acetic acid, succinic acid, tartaric acid, methane-sulfonic acid, p-toluenesulfonic acid and the like.

Preferred compounds of formula I in the scope of the present invention are those, wherein n is 2 and $R^1$ and $R^3$ are hydrogen. These are the following compounds:

(RS)-3-[4-(3,4-dihydro-1H-isoquinolin-2-yl)-quinolin-2-ylamino]-propane-1,2-diol, (S)-1-[4-(3,4-dihydro-1H-isoquinolin-2-yl)-quinolin-2-ylamino]-propan-2-ol,
4-(3,4-dihydro-1H-isoquinolin-2-yl)-quinolin-2-ylamine and
4-(3,4-dihydro-1H-isoquinolin-2-yl)-quinolin.

Compounds of the present invention, in which n is 1, $R^1$ is hydrogen and $R^3$ is hydrogen or halogen, are further preferred, for example the following compounds:
4-(5-chloro-1,3-dihydro-isoindol-2-yl)-quinoline and
4-(1,3-dihydro-isoindol-2-yl)-quinoline.

In other compounds, $R^1$ and $R^3$ are hydrogen and $R^2$ is —NHCH$_2$CH(OH)R or amino, and preferably n is 2. In yet other compounds, $R^1$ and $R^3$ are hydrogen, and preferably n is 1. In other compounds, $R^1$ is lower alkoxy (especially methoxy) and $R^3$ is hydrogen, and n is preferably 2.

The afore-mentioned compounds of formula I can be manufactured in accordance with the invention by a) reacting a compound formula

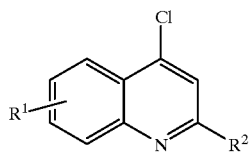

II with an amine of formula

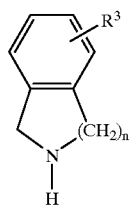

III to a compound of formula

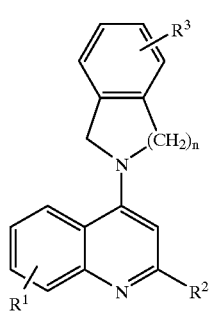

I wherein $R^1$—$R^3$ and n have the significances given above, or b) reacting a compound of formula

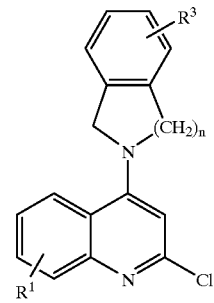

IV with a compound of formula

HR$^2$   V, wherein $R^1$ to $R^3$ and n have the significances given above with the exception that $R^2$ is not hydrogen, lower alkyl or amino, to give a compound of formula I, and if desired, modifying one or more substituents within the definitions given above, or if desired, converting the compound of formula I obtained into a pharmaceutically acceptable salt.

In the following the preparation of compounds of formula I are described in more detail: In accordance with the process variants, described above, and with the scheme 1, described below, compounds of formula I may be prepared by known procedures, for example the following by reaction at 150–160° C. of a 2-chloro-4-(3,4-dihydro-1H-isoquinolin-2-yl) or a 2-chloro-4-(1,3-dihydro-isoindol-2-yl)-quinoline with a primary or secondary amine using the neat amine as solvent, or by reaction of 140–150° C. of a 4-chloro-quinoline with a 1,2,3,4-tetrahydroisoquinoline or a 2,3-dihydro-1H-isoindole in a stoechiometric fashion.

2-Chloro-4-(3,4-dihydro-1H-isoquinolin-2-yl)-quinolines and 2-chloro-4-(1,3-dihydro-isoindol-2-yl)-quinolines were prepared using known methods (Curd, F. H. S.; Raison, C. G.; Rose, F. L.; J. Chem. Soc. 1947, 899) by reacting a 2,4-dihydroxy-quinoline with a 1,2,3,4-tetrahydroisoquinoline or a 2,3-dihydro-1H-isoindole at 200° C. followed by a treatment with a chlorinating agent like phosphorous oxychloride.

4-Chloro-quinolines were prepared using known methods by reacting the corresponding quinolin-4-ones with a chlorinating agent like phosphorous oxychloride (scheme 1)

Scheme 1

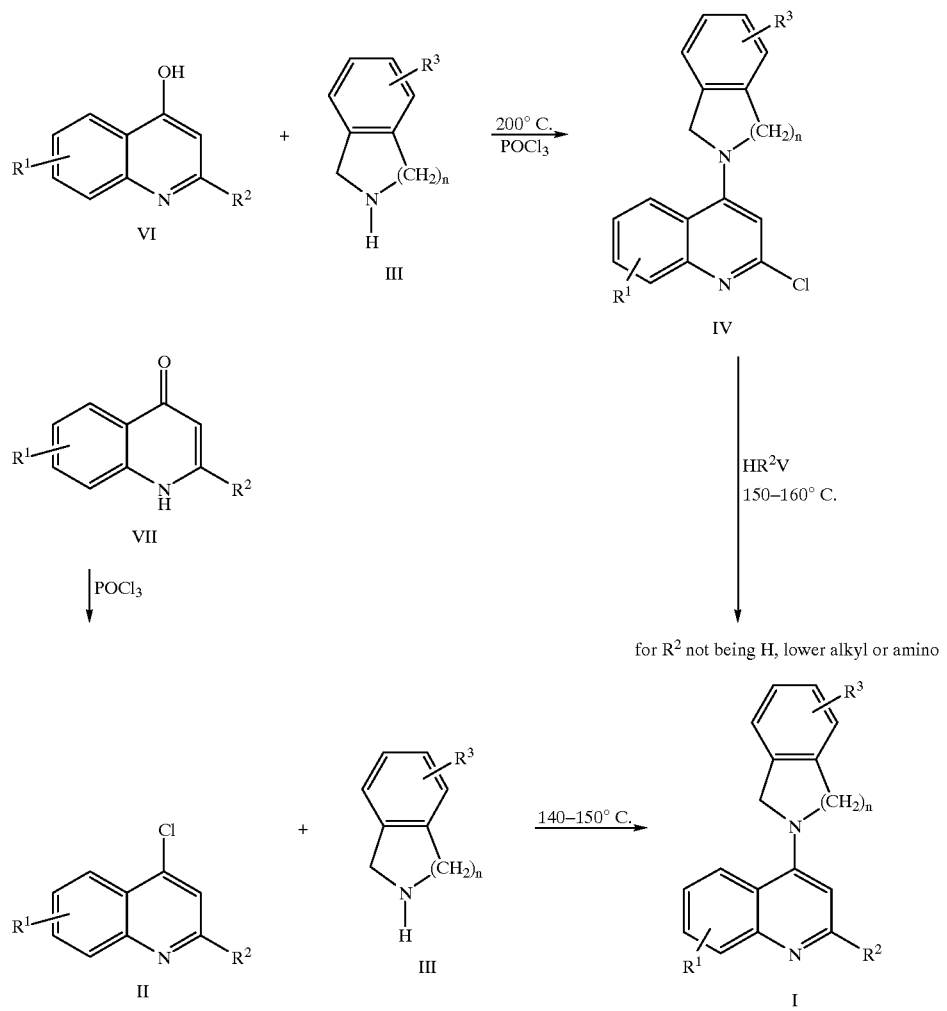

Pharmaceutically acceptable salts can be manufactured according to methods which are known per se and familiar to any person skilled in the art. The acid addition salts of compounds of formula I are especially well suited for pharmaceutical use.

In scheme 1 are described process for preparation of compounds of formula I, starting from known compounds, from commercial products or from compounds, which can be prepared in conventional manner.

The preparation of compounds of formula I are described in more detail in working examples 1–18.

As mentioned earlier, the compounds of formula I and their pharmaceutically usable acid addition salts possess valuable pharmacodynamic properties. They are NMDA-receptor subtype selective blockers, which have a key function in modulating neuronal activity and plasticity which makes them key players in mediating processes underlying development of CNS as well as learning and memory function.

The compounds were investigated in accordance with the test given hereinafter.

Test method $^3$H-[R-(R*,S*)]-a-(4-Hydroxy-phenyl)-b-methyl-4-(phenyl-methyl)-1-piperidine propanol binding Male Füllinsdorf albino rats weighing between 150–200 g were used. Membranes were prepared by homogenization of the whole brain minus cerebellum and medulla oblongata with a Polytron (10.000 rpm, 30 seconds), in 25 volume of a cold Tris-HCl 50 mM, EDTA 10 mM, pH 7.1 buffer. The homogenate was centrifuged at 48,000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.5 cold buffer. The final pellet was resuspended in the same buffer and used at a final concentration of 200 mg of protein/ml.

[R-(R*,S*)]-α-(4-Hydroxy-phenyl)-β-methyl-4-(phenyl-methyl)-1-piperidine propanol is a compound known to bind selectively to the NMDA receptor (J. Neurochem., Vol. 70., No. 5, 1998). $^3$H-[R-(R*,S*)]-α-(4-Hydroxy-phenyl)-β-methyl-4-(phenyl-methyl)-1-piperidine propanol binding experiments were performed using a Tris-HCl 50 mM, pH 7.4 buffer. For displacement experiments 5 nM of 3H-[R-(R*,S*)]-a-(4-hydroxy-phenyl)-b-methyl-4-(phenyl-methyl)-1-piperidine propanol were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits.

The $IC_{50}(\mu M)$ of preferred compounds of formula I, tested in accordance with the above mentioned methods, is <1 $\mu M$.

Examples of some $IC_{50}$ values are given in the table below:

| Example | $IC_{50}$ ($\mu M$) |
|---|---|
| 2 | 0.058 |
| 4 | 0.17 |
| 5 | 0.29 |
| 13 | 0.19 |
| 15 | 0.32 |
| 16 | 0.65 |
| 18 | 0.89 |

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances. Thus part of this invention is a pharmaceutical composition comprising a compound of formula I, in particular a preferred compound as described above, or a pharmaceutically acceptable salt thereof and an inert carrier.

Also part of this invention is a method for treating neurodegeneration resulting from NMDA receptor activation which comprises administering an amount of compound of formula I effective to alleviate the neurodegeneration. The dosage can vary within wide limits and will, of course, be fitted to the individual requirements in each particular case. In the case of oral administration the dosage lies in the range of about 0.1 mg per dosage to about 1000 mg per day of a compound of formula I although the upper limit can also be exceeded when this is shown to be indicated. An amount effective to alleviate the neurodegeneration depends on the individual, however alleviation occurs when the condition in question exhibits either symptomatic improvement or improvement according to an accepted assay.

The following examples illustrate the present invention in more detail. However, they are not intended to limit its scope in any manner. All temperatures are given in degree Celsius.

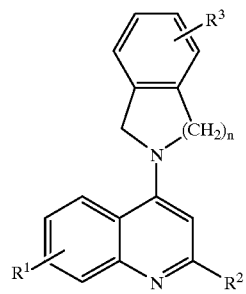

I

| $R^1$ | $R^2$ | $R^3$ | n | Example No. |
|---|---|---|---|---|
| H | NHCH$_2$CH(OH)CH$_2$OH | H | 2 | 1 |
| H | NH(CH$_2$)$_2$OH | H | 2 | 2 |
| H | NHCH$_2$CH(OH)CH$_3$ | H | 2 | 3 |
| H | (N-methyl-pyrrolidin-3-ol) | H | 2 | 4 |
| H | (N-methyl-2-hydroxymethyl-pyrrolidine) | H | 2 | 5 |
| H | H | 5-Cl | 1 | 6 |
| H | H | H | 1 | 7 |
| H | NH$_2$ | H | 2 | 8 |
| H | H | H | 2 | 9 |
| 6-OCH$_3$ | H | H | 2 | 10 |
| 7-OCH$_3$ | H | H | 2 | 11 |
| 8-OCH$_3$ | H | H | 2 | 12 |
| 7-CH$_3$ | H | H | 2 | 13 |
| H | CH$_3$ | H | 2 | 14 |
| 7-Cl | H | H | 2 | 15 |
| 8-F | H | H | 2 | 16 |
| 6-OH | H | H | 2 | 17 |
| 6-F | H | H | 2 | 18 |

EXAMPLE 1

(RS)-3-[4-(3,4-Dihydro-1H-isoquinolin-2-yl)-quinolin-2-ylamino]-propane-1,2-diol hydrochloride 2-Chloro-4-(3,4-dihydro-1H-isoquinolin-2-yl)-quinoline (0.44 g, 1.5 mmol) and (RS)-3-amino-1,2-propanediol (0.82 g, 9.0 mmol) were mixed and heated at 150–160° C. for 5 hours. The reaction mixture was cooled to room temperature and water (15 ml) was added. The resulting solid was filtered, dried and chromatographed over silica gel (CH$_2$Cl$_2$—MeOH, 19:1 then 9:1) to provide a white foam which was dissolved in MeOH. HCl—Et$_2$O was added to provide (RS)-3-[4-(3,4-dihydro-1H-isoquinolin-2-yl)-quinolin-2-ylamino]-propane-1,2-diol hydrochloride (0.4 g, 69%) as an offwhite foam, MS: m/=349 (M$^+$).

Following the general method of example 1 the compounds of example 2 to example 5 were prepared.

EXAMPLE 2

2-[4-(3,4-Dihydro-1H-isoquinolin-2-yl)-quinolin-2-ylamino]-ethanol hydrochloride The title compound, MS: m/e=320.3 (M+H$^+$), was prepared from 2-chloro-4-(3,4-dihydro-1H-isoquinolin-2-yl)-quinoline and ethanolamine.

EXAMPLE 3

(S)-1-[4-(3,4-Dihydro-1H-isoquinolin-2-yl)-quinolin-2-ylamino]-propan-2-ol hydrochloride The title compound, MS: m/e=334.3 (M+H$^+$), was prepared from 2-chloro-4-(3,4-dihydro-1H-isoquinolin-2-yl)-quinoline and S(+)-1amino-2-propanol.

EXAMPLE 4

(R)-1-[4-(3,4-Dihydro-1H-isoquinolin-2-yl)-quinolin-2-yl]-pyrrolidin-3-ol hydrochloride The title compound, m.p. 270–274° C., $[\alpha]_D^{20}$ =−34° (c=0.54, methanol) and MS: m/e=346.3 (M+H$^+$), was prepared from 2-chloro-4-(3,4-dihydro-1H-isoquinolin-2yl)-quinoline and (R)-3-hydroxypyrrolidine

EXAMPLE 5

(R)-{1-[4-(3,4-Dihydro-1H-isoquinolin-2-yl)-quinolin-2-yl]-pyrrolidin-2-yl}-methanol The title compound, m.p. 74–80° C., $[\alpha]_D^{20}$ =30 63.2° (c=0.53, methanol) and MS: m/e=360.3 (M+H$^+$), was prepared from 2-chloro-4-(3,4-dihydro-1H-isoquinolin-2-yl)-quinoline and D-prolinol.

EXAMPLE 6

4-(5-Chloro-1,3-dihydro-isoindol-2-yl)quinoline hydrochloride

A mixture of 4-chloroquinoline (0.245 g, 1.5 mmol) and 5-Chloro-2,3-dihydro-1H-isoindole (0.23 g, 1.5 mmol) was heated at 140–150° C. for 4 hours under Argon then cooled to room temperature. The crude product was recrystallized with methanol to provide 4-(5-Chloro-1,3-dihydro-isoindol-2-yl)-quinoline hydrochloride (0.115 g, 24%) as white solid, m.p. 270–275° C. and MS: m/e=280 (M$^+$).

5-Chloro-2,3-dihydro-1H-isoindole is a known compound and has been prepared as described in the following reference: EP 343560

Following the general method of Example 6 the compounds of Example 7 to Example 18 were prepared.

EXAMPLE 7

4-(1,3-Dihydro-isoindol-2-yl)-quinoline hydrochloride

The title compound m.p. 264–267° C. and MS: m/e=247.3 (M+H$^+$), was prepared from 4-chloroquinoline and 2,3-dihydro-1H-isoindole.

EXAMPLE 8

4-(3,4-Dihydro-1H-isoquinolin-2-yl)-quinolin-2-ylamine

The title compound, MS: m/e=276.3 (M+H$^+$), was prepared from 4-chloro-quinolin-2-ylamine and 1,2,3,4-tetrahydroisoquinoline.

EXAMPLE 9

4-(3,4-Dihydro-1H-isoquinolin-2-yl)-quinoline hydrochloride

The title compound, m.p. 200° C., and MS: m/e=260 (M$^+$), was prepared from 4-chloro-quinoline and 1,2,3,4-tetrahydroisoquinoline

EXAMPLE 10

The title compound, m.p. 218–219° C., and MS: m/e=291.2 (M+H$^+$), was prepared from 4-chloro-6-methoxy-quinoline and 1,2,3,4-tetrahydroisoquinoline.

EXAMPLE 11

4-(3,4-Dihydro-1H-isoquinolin-2-yl)-7-methoxy-quinoline hydrochloride

The title compound, MS: m/e=291.2 (M+H$^+$), was prepared from 4-chloro-7-methoxy-quinoline and 1,2,3,4-tetrahydroisoquinoline

EXAMPLE 12

4-(3,4-Dihydro-1H-isoquinolin-2-yl)-8-methoxy-quinoline hydrochloride

The title compound, m.p. 240° C. MS: m/e=291.2 (M+H$^+$), was prepared from 4-chloro-8-methoxy-quinoline and 1,2,3,4-tetrahydroisoquinoline.

EXAMPLE 13

4-(3,4-Dihydro-1H-isoquinolin-2-yl)-7-methyl-quinoline hydrochloride

The title compound, m.p. 251–252° C. MS: m/e=275.3 (M+H$^+$), was prepared from 4-chloro-7-methyl-quinoline and 1,2,3,4-tetrahydroisoquinoline.

EXAMPLE 14

4-(3,4-Dihydro-1H-isoquinolin-2-yl)-2-methyl-quinoline hydrochloride

The title compound, m. p. 210–211° C. MS: m/e=275.3 (M+H$^+$), was prepared from 4-chloroquinaldine and 1,2,3,4-tetrahydroisoquinoline.

EXAMPLE 15

7-Chloro-4-(3,4-dihydro-1H-isoquinolin-2-yl)-quinoline hydrochloride

The title compound, MS: m/e=295.3 (M+H$^+$), was prepared from 4,7-dichloroquinoline and 1,2,3,4-tetrahydroisoquinoline.

EXAMPLE 16

4-(3,4-Dihydro-1H-isoquinolin-2-yl)-8-fluoro-quinoline hydrochloride

The title compound, MS: m/e=279.2 (M+H$^+$), was prepared from 4-chloro-8-fluoroquinoline and 1,2,3,4-tetrahydroisoquinoline.

EXAMPLE 17

4-(3,4-Dihydro-1H-isoquinolin-2-yl)-quinolin-6-ol hydrochloride

The title compound, MS: m/e=277.2 (M+H$^+$), was prepared 4-chloro-quinolin-6-ol and 1,2,3,4-tetrahydroisoquinoline.

EXAMPLE 18

4-(3,4-Dihydro-1H-isoquinolin-2-yl)-6-fluoro-quinoline hydrochloride

The title compound, MS: m/e=279.2 (M+H$^+$), was prepared 4-chloro-6-fluoroquinoline and 1,2,3,4-tetrahydroisoquinoline.

EXAMPLE A

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 835 |

Manufacturing Procedure

1 Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE B

Capsule Formulation

| | | mg/capsule | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1 Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:
1. Compounds of formula

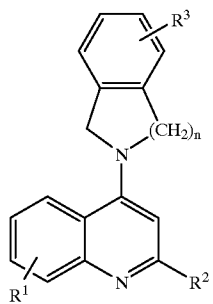

I wherein
$R^1$ is hydrogen, lower alkyl, lower alkoxy, hydroxy, amino, nitro, cyano, lower alkyl-amino, di-lower alkyl-amino or halogen;

$R^2$ is hydrogen, lower alkyl, amino, pyrrolidin-3-ol, pyrrolidin-2-yl-methanol or —NHCH$_2$CH(OH)R;

$R^3$ is hydrogen or halogen;

R is hydrogen, lower alkyl or —CH$_2$OH;

n is 1 or 2;

and pharmaceutically acceptable acid addition salts thereof.

2. Compounds of claim 1, wherein n is 2 and $R^1$ and $R^3$ are hydrogen.

3. Compounds of claim 2, which are (RS)-3-[4-(3,4-dihydro-1H-isoquinolin-2-yl)-quinolin-2-ylamino]-propane-1,2-diol, (S)-1-[4-(3,4-dihydro-1H-isoquinolin-2-yl)-quinolin-2-ylamino]-propan-2-ol, 4-(3,4-dihydro-1H-isoquinolin-2-yl)-quinolin-2-ylamine and 4-(3,4-dihydro-1H-isoquinolin-2-yl)-quinoline.

4. Compounds of claim 1, wherein n is 1 and $R^1$ is hydrogen and $R^3$ is hydrogen or halogen.

5. Compounds of claim 4, which are
4-(5-chloro-1,3-dihydro-isoindol-2-yl)-quinoline and
4-(1,3-dihydro-isoindol-2-yl)-quinoline.

6. Compounds of claim 1, wherein $R^1$ and $R^3$ are hydrogen and $R^2$ is —NHCH$_2$CH(OH)OH or amino.

7. Compounds of claim 6 wherein n is 2.

8. Compounds of claim 1, wherein $R^1$ and $R^3$ are hydrogen.

9. Compounds of claim 8, wherein n is 1.

10. Compounds of claim 1, wherein $R^1$ is lower alkoxy and $R^3$ is hydrogen.

11. Compounds of claim 10, wherein n is 2.

12. A pharmaceutical composition comprising a compound of formula I or a pharmaceutically acceptable salt thereof and an inert carrier.

13. A pharmaceutical composition wherein the compound of formula I is (RS)-3-[4-(3,4-dihydro-1H-isoquinolin-2-yl)-quinolin-2-ylamino]-propane-1,2-diol, (S)-1-[4-(3,4-dihydro-1H-isoquinolin-2-yl)-quinolin-2-ylamino]-propan-2-ol, 4-(3,4-dihydro-1H-isoquinolin-2-yl)-quinolin-2-ylamine, 4-(3,4-dihydro-1H-isoquinolin-2-yl)-quinolin, 4-(5-chloro-1,3-dihydro-isoindol-2-yl)-quinolin, or 4-(1,3-dihydro-isoindol-2-yl)-quinoline.

14. A method for treating neurodegeneration resulting from NMDA receptor activation which comprises administering an amount of a compound of formula I effective to alleviate the neurodegeneration.

15. The method of claim 14, wherein the compound of formula I is (RS)-3-[4-(3,4-dihydro-1H-isoquinolin-2-yl)-quinolin-2-ylamino]-propane-1,2-diol, (S)-1-[4-(3,4-dihydro-1H-isoquinolin-2-yl)-quinolin-2-ylamino]-propan-2-ol, 4-(3,4-dihydro-1H-isoquinolin-2-yl)-quinolin-2-ylamine, 4-(3,4-dihydro-1H-isoquinolin-2-yl)-quinolin, 4-(5-chloro-1,3-dihydro-isoindol-2-yl)-quinoline, or 4-(1,3-dihydro-isoindol-2-yl)-quinoline.

* * * * *